US00PP27746P3

(12) United States Plant Patent
Sills et al.

(10) Patent No.: US PP27,746 P3
(45) Date of Patent: Mar. 7, 2017

(54) BLACKBERRY PLANT NAMED 'DRISBLACKTWELVE'

(50) Latin Name: ***Rubus* L. subgenus *Rubus***
Varietal Denomination: DrisBlackTwelve

(71) Applicant: Driscoll's, Inc., Watsonville, CA (US)

(72) Inventors: Gavin R. Sills, Gilroy, CA (US); Andrea M. Pabon, Gilroy, CA (US); Mark Crusha, Capitola, CA (US)

(73) Assignee: Driscoll's, Inc., Watsonville, CA (US)

( * ) Notice: Subject to any disclaimer, the term of this patent is extended or adjusted under 35 U.S.C. 154(b) by 32 days.

(21) Appl. No.: 14/544,300

(22) Filed: Dec. 19, 2014

(65) Prior Publication Data

US 2016/0183425 P1 Jun. 23, 2016

(51) Int. Cl.
*A01H 5/08* (2006.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| 2016/0183424 | P1 | 6/2016 | Sills et al. |
| 2016/0249505 | P1 | 8/2016 | Sills et al. |

OTHER PUBLICATIONS

Sills et al., U.S. Appl. No. 14/999,063, filed Mar. 25, 2016, titled "Blackberry plant named DrisBlackSixteen".
Voss, Donald H., "The Royal Horticultural Society Colour Chart 2001", Journal American Rhododendron Society, vol. 56, No. 1, 2001, 3 pages.
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Keith Robinson
(74) *Attorney, Agent, or Firm* — Morrison & Foerster LLP

(57) ABSTRACT

This invention relates to a new and distinct variety of blackberry plant named 'DrisBlackTwelve', particularly characterized by having medium to high vigor, medium-sized, black fruit and medium to high yield, is disclosed.

2 Drawing Sheets

Genus and species: *Rubus* L. subgenus *Rubus*.
Variety denomination: 'DrisBlackTwelve'.

BACKGROUND OF THE NEW PLANT

The present invention relates to a new and distinct blackberry cultivar designated 'DrisBlackTwelve' and botanically known as *Rubus* L. subgenus *Rubus*. This new blackberry variety was identified in Santa Cruz County, Calif. in June 2008 and originated from a cross between the proprietary female parent blackberry plant 'BM711 (858A5)' (unpatented) and the proprietary male parent blackberry plant 'BJ111.1' (unpatented). The original seedling of the new cultivar was first asexually propagated by tissue culture and root cuttings at a nursery in Santa Cruz County, Calif. 'DrisBlackTwelve' was subsequently asexually propagated by tissue culture and root cuttings and underwent further testing at a nursery in Santa Cruz County, Calif. from 2012 to 2014. The present invention has been found to be stable and reproduce true to type through successive asexual propagations.

SUMMARY OF THE INVENTION

The following are the most outstanding and distinguishing characteristics of this new cultivar when grown under normal horticultural practices in Santa Cruz County, Calif.

1. Medium to high vigor;
2. Medium-sized, black berries; and
3. Medium to high yield.

DESCRIPTION OF THE PHOTOGRAPHS

This new blackberry plant is illustrated by the accompanying photographs which show the plant's canes, flowers, fruit, and leaves. The colors shown are as true as can be reasonably obtained by conventional photographic procedures. The photographs are of plants that are 2 years old.

DESCRIPTION OF THE NEW VARIETY

Figure 1:
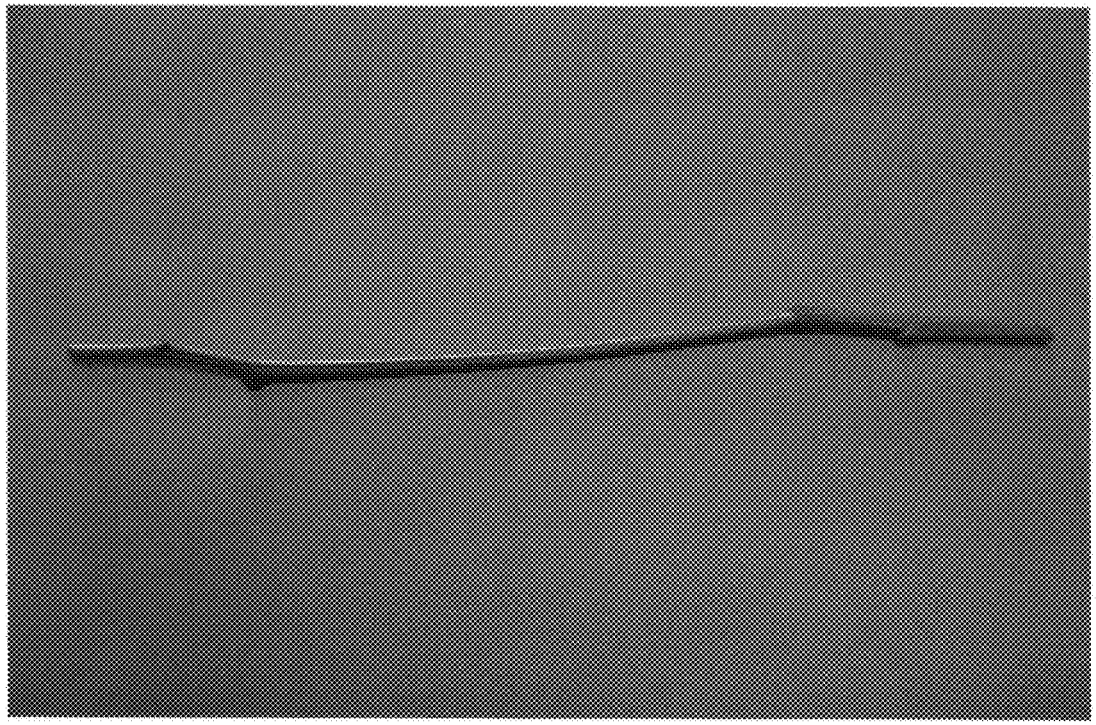
FIG. 1 shows a section of a young cane without spines.
Figure 2:
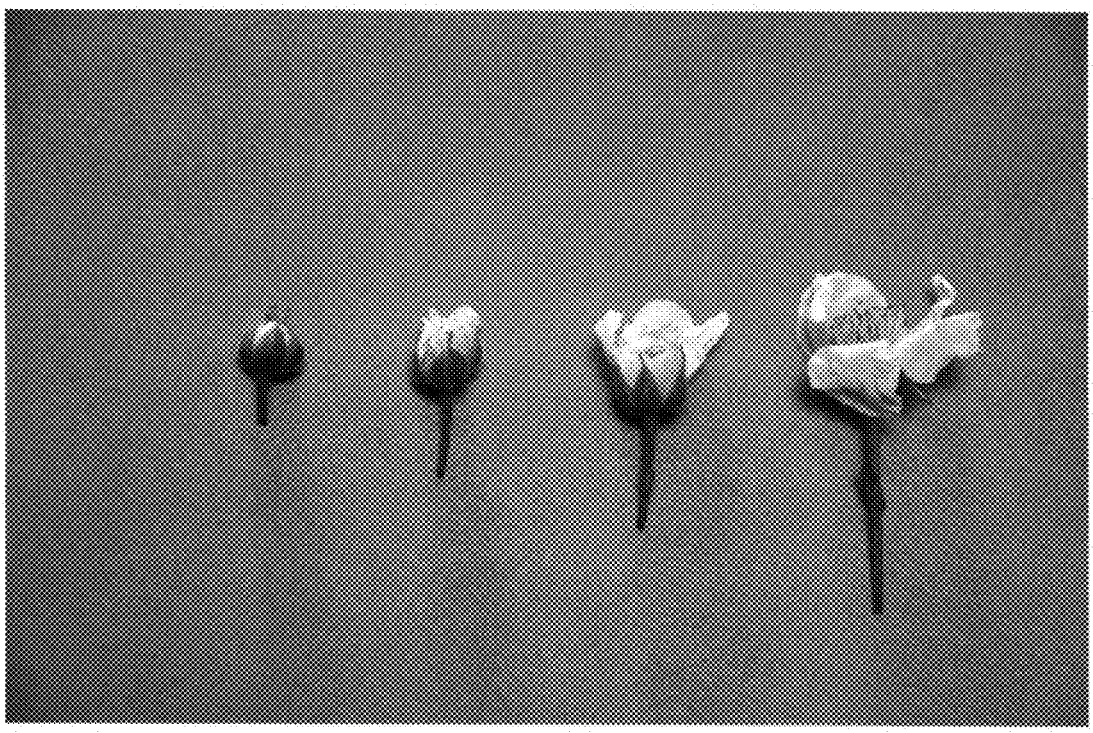
FIG. 2 shows the flowers at various stages.
Figure 3:
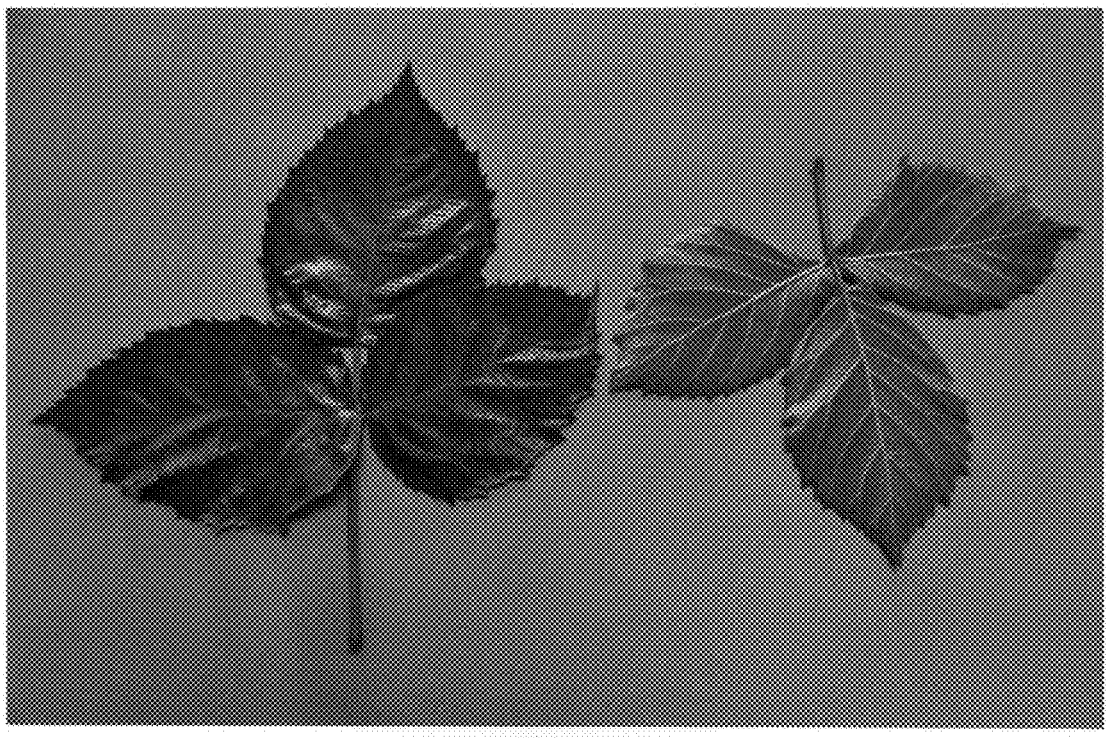
FIG. 3 shows the upper and lower surfaces of the leaves.

The following descriptions of 'DrisBlackTwelve' are based on observations made in Santa Cruz County, Calif. on 2-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackTwelve' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* 2$^{nd}$ edition, by James G. Harris and Melinda Woolf Harris, unless where otherwise defined.

DETAILED BOTANICAL DESCRIPTION

Classification:

*Family*.—Rosaceae.

*Botanical*.—*Rubus* L. subgenus *Rubus*.

*Common name*.—Blackberry.

*Variety name*.—'DrisBlackTwelve'.

Parentage:

*Female parent*.—Proprietary blackberry plant named 'BM711 (858A5)' (unpatented).

*Male parent*.—Proprietary blackberry plant named 'BJ111.1' (unpatented).

Plant:

*Vigor*.—Medium to high.

*Growth habit*.—Upright to semi-upright.

*Productivity*.—Medium.

*Propagation*.—Tissue culture and root cuttings.

*Self-fruitfulness*.—Partially self-fruitful.

*Time of bud burst*.—March.

Canes:

*Fruiting lateral length* (4$^{th}$ *lateral from tip*).—Medium; 34.8 cm.

*Number of fruit per lateral*.—12.

*Fruiting on current year's cane*.—Present.

*Cane internodal distance*.—6.2 cm.

*Number of new canes during flowering*.—5-6.

*New cane strength* (*observed full-grown shoot after picking*).—Medium.

*Glaucosity observed on full-grown shoot after picking*.—Medium.

*Young shoots*.—Quantity: 5-6. Time of emergence from soil: February. Anthocyanin coloration (during rapid growth): Medium; RHS 183A (Dark greyed-purple). Intensity of green color: Medium; RHS 144A (Medium yellow-green).

*Dormant cane*.—Length: 4-5 ft pruned. Diameter (in central third): 1.0-1.5 cm. Cross section (from mid cane observed at end of first growing season): Rounded to angular. Color: RHS 148B (Medium yellow-green). Number of branches: 20-23. Distribution of branches: Only on upper half. Anthocyanin coloration: Medium; RHS 143A (Medium green). Spines: Absent.

Leaves:

*Type*.—Palmate.

*Predominant number of leaflets*.—Five.

*Overlapping or relative position of lateral leaflets*.—Overlapping.

*Color*.—Upper surface: Dark; RHS 137A (Dark green). Lower surface: Medium; RHS 144B (Medium yellow-green).

*Glossiness of upper side*.—Weak to medium.

*Cross section profile*.—Convex (margins rolled backwards).

*Leaflets*.—Shape: Ovate. Margin: Doubly serrate. Depth of incisions: 2-5 cm. Type of incision margin: Bi-serrate. Apex: Truncate. Base: Obtuse. Rachis length between terminal leaflet and adjacent lateral leaflet: 54.6 mm.

*Lateral leaflet* (*basal pair*).—Length: 127.6 mm. Width: 89.1 mm. Length/width ratio: 1.4.

*Terminal leaflet*.—Length: Medium; 139.8 mm. Width: Medium; 107.6 mm. Length/width ratio: 1.3. Lobing: Absent. Undulation of margin (rippling of margin): Medium. Blistering between veins (rugosity): Medium. Shape: Ovate. Tip: Truncate. Base: Obtuse. Margin: Doubly serrate. Cross-section: U-shaped.

*Petiole*.—Length: 29.3 mm. Diameter: 2.5 mm. Pigmentation: Upper surface: Medium; RHS 157C (Green white). Lower surface: Medium; RHS 157C (Green white). Color: RHS 144A (Medium yellow-green).

*Stipule*.—Size: Length of 7-12 mm and width of 1 mm. Orientation: Clasping. Color: RHS 143C (Strong yellow-green).

Inflorescence:

*Time of beginning of flowering on current year's cane*.—June-August.

*Flower diameter*.—2-3 cm.

*Flower number* (*at* 3$^{rd}$ *node from tip of lateral*).—2.

*Petal*.—Length: 21.89 mm. Width: 16.84 mm. Length/width ratio: 1.3. Color: RHS 155D (White).

*Pedicel*.—Length: 53.47 mm. Diameter: 1.56 mm. Color: RHS 143A (Medium green).

Fruit:

*Length*.—Medium; 32.66 mm.

*Width*.—Medium; 25.30 mm.

*Ratio of length to width*.—Medium to large; 1.3.

*Size*.—Medium.

*Glossiness*.—Medium to strong.

*Shape in longitudinal section*.—Medium ovate.

*Weight* (*g/fruit*).—9.94 g.

*Soluble solids* (%) (*in Brix*).—9.3.

*Titratable acidity*.—(% as citric acid): 0.91.

*Seed weight* (*g/seed*).—0.005176.

*Number of drupelets/fruit*.—Medium; 100.95.

*Firmness*.—Medium.

*Color*.—Immature: RHS 144A (Medium yellow-green). Maturing: RHS 60B (Dark red-purple). Mature: RHS 203A (Black).

*Time of ripening on current year's cane*.—July-October.

*Harvest interval*.—Mid-August-mid-November.

*Yield*.—Total yield from plants that were two-years old or older ranged from 9,200 lb/acre to 41,100 lb/acre during a three year period when grown in Watsonville, Calif.

Disease, pest, and stress resistance: Not tested.

COMPARISON WITH PARENTAL AND COMMERCIAL VARIETIES

'DrisBlackTwelve' differs from the proprietary female parent 'BM711 (858A5)' (unpatented) in that 'DrisBlackTwelve' is thornless, whereas 'BM711 (858A5)' has thorns.

'DrisBlackTwelve' differs from the proprietary male parent 'BJ111.1' (unpatented) in that 'DrisBlackTwelve' has larger fruit and later production than 'BJ111.1'.

'DrisBlackTwelve' differs from the commercial variety 'DrisBlackNine' (U.S. Plant Pat. No. 26,774) in that 'DrisBlackTwelve' has an upright to semi-upright growth habit, palmate type leaves and medium ovate shaped fruit, whereas 'DrisBlackNine' has an upright growth habit, intermediate type leaves and oblong shaped fruit. Additionally, 'DrisBlackTwelve' has medium to large sized drupelets, whereas 'DrisBlackNine' has small to medium sized drupelets.

'DrisBlackTwelve' differs from commercial variety 'DrisBlackTen' (U.S. Plant Pat. No. 26,611) in that 'DrisBlackTwelve' has medium productivity and palmate type leaves, whereas 'DrisBlackTen' has high productivity and odd-pinnate type leaves. Additionally, 'DrisBlackTwelve' has medium to strongly glossy, medium sized fruit, whereas 'DrisBlackTen' has medium glossy, large sized fruit.

We claim:

1. A new and distinct variety of blackberry plant named 'DrisBlackTwelve', substantially as described and illustrated herein.

* * * * *